(12) United States Patent
Iovdalsky et al.

(10) Patent No.: US 6,202,467 B1
(45) Date of Patent: Mar. 20, 2001

(54) HYBRID INTEGRATED CIRCUIT FOR A GAS SENSOR

(75) Inventors: Viktor Anatolievich Iovdalsky; Igor Mikhailovich Olikhov; Ilya Markovich Bleivas; Vladimir Mikhailovich Ipolitov, all of Moskovskaya obl. (RU)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 09/091,255

(22) PCT Filed: Oct. 10, 1996

(86) PCT No.: PCT/RU96/00291

§ 371 Date: Jul. 26, 1999

§ 102(e) Date: Jul. 26, 1999

(87) PCT Pub. No.: WO98/15818

PCT Pub. Date: Apr. 16, 1998

(51) Int. Cl.[7] .......................... G01N 27/12; G01N 27/04; H01L 7/00
(52) U.S. Cl. ................ 73/23.2; 73/25.05; 73/31.05; 422/88; 422/94
(58) Field of Search ................... 73/23.2, 31.05, 73/25.05, 31.02, 31.06; 422/83, 88, 95

(56) References Cited

U.S. PATENT DOCUMENTS

| | | | |
|---|---|---|---|
| 4,347,732 | * | 9/1982 | Leary ........................... 73/23 |
| 4,580,439 | * | 4/1986 | Manaka ....................... 73/23 |
| 4,596,975 | * | 6/1986 | Reddy et al. ................ 338/34 |
| 4,706,493 | * | 11/1987 | Chang et al. ................ 73/23 |
| 4,792,433 | * | 12/1988 | Katsura et al. .............. 422/98 |
| 4,928,513 | * | 5/1990 | Sugihara et al. ............. 73/1 G |
| 4,984,446 | * | 1/1991 | Yagawara et al. .......... 73/31.06 |
| 4,991,424 | * | 2/1991 | Lehto ........................ 73/31.06 |
| 5,321,971 | * | 6/1994 | Hobbs et al. ............... 73/23.2 |
| 5,367,283 | * | 11/1994 | Lauf et al. .................. 338/34 |
| 5,605,612 | * | 2/1997 | Park et al. .................. 204/429 |
| 5,659,127 | * | 8/1997 | Shie et al. .................. 73/31.05 |
| 5,707,148 | * | 1/1998 | Visser et al. ............... 374/31 |
| 5,744,697 | * | 4/1998 | Martell et al. ............. 73/31.06 |
| 5,786,608 | * | 7/1998 | Lescouzeres et al. ....... 257/253 |
| 5,811,662 | * | 9/1998 | Williams et al. ........... 73/31.06 |
| 5,821,402 | * | 10/1998 | Okajima et al. ........... 73/23.2 |
| 5,866,800 | * | 2/1999 | Park et al. ................. 73/31.06 |

* cited by examiner

Primary Examiner—Hezron Williams
Assistant Examiner—David J. Wiggins
(74) Attorney, Agent, or Firm—Piper Marbury Rudnick & Wolfe; William T. Rifkin; Michael L. Kenaga

(57) ABSTRACT

A hybrid integrated circuit of a gas sensor, comprising a substrate (1) in the form of a ring-shaped peripheral portion (2) and a disk-shaped central portion (3), both being interconnected through three jumpers (4) spaced 120° apart and having three branchings (10) arranged at 120° at the peripheral portion (2). The central portion (3) carries a gas-sensitive film (7), a film heater (6), and a film electrode (8) of the circuit for measuring the resistance of the gas-sensitive film (7). The heater (6) and the electrode (8) are electrically connected along the jumpers (4) to bonding pads (5) located in the peripheral portion (2). The thickness of the jumpers (4) and of the central portion (3) is 0.15–0.25 mm, and the width of the jumpers (4) is 0.05–0.15 mm.

3 Claims, 3 Drawing Sheets

HYBRID INTEGRATED CIRCUIT FOR A GAS SENSOR

FIELD OF THE INVENTION

The present invention relates in general to electronic engineering and more specifically it concerns design technology for building a hybrid integrated circuit of a gas sensor.

BACKGROUND OF THE INVENTION

A thermochemical sensing transducer is known detecting the presence and concentration of various gases in the air such as air including $CH_3$ or Hydrogen. The known sensing transducer of prior arts provides a higher measuring accuracy due to the layer of a catalyst (platinum, palladium, or metal oxides) applied to the external surface of the sensing element, and an extended range of gases monitored which is due to the fact the sensing elements are made of different materials, have different dimensions, and make use of different catalysts. Two silicon stages are installed independently on the same substrate for two constructionally similar sensing elements (save the aforementioned basic differences). An insulating nitride layer 400 mm thick is applied to the silicon membrane of the stage. A double-meander heater is established at the center of the sensing element, said heater being made of silicon or nickel and having aluminium electric leads to the sensing element periphery. A thermocouple consisting of two meanders connected in opposition and made of different materials is applied to the heater in perpendicular with the axis thereof. A catalyst layer is applied from above, which may be coated with a protective gas-permeable layer. The aforecited sensing transducer is capable of measuring concentration variations with temperature (DE, A, 4,008,150).

However, the aforementioned construction is sophisticated and inadequately technologically manufacturable.

A structure for the gas analyzer carrier is known from prior arts, said structure enabling to obtain a mechanically strong construction of analyzers for such gases as $SO_2$, $H_2S$, and benzene suitable for the large-scale production. The construction of said structure appears as a square of 6×6 mm inside which another square of 2×2 mm is placed, both squares being interconnected with jumpers along the four diagonals common to both squares. The central square and partly two opposite jumpers are coated with a layer of platinum serving as a heater. The central square-shaped platinum coating is shaped as a spiral. The resultant resistor is coated with an insulating layer. Two electrodes made of platinum or gold are applied to the opposite sides of the central square, two metal strip electrodes directed along the free substrate jumpers being connected to said platinum or gold electrodes. A gas-sensitive film is applied to the central square between the electrodes (FR, A, 2,625,561).

However, the construction discussed above is sophisticated difficult to assemble, has no adequate selectivity due to an insufficient heat insulation of the central substrate portion, and is possessed of inadequate manufacturability.

SUMMARY OF THE INVENTION

The principal object of the present invention is to provide a hybrid integrated circuit of a gas sensor having such a constructive arrangement that allows to increase the selectivity, thermal isolation, and manufacturability of the gas sensor.

The foregoing object is accomplished due to the fact that in a hybrid integrated circuit of a gas sensor, comprising a substrate in the form of a mechanically strong peripheral portion and a central portion thermally insulated therefrom, both portions being interconnected through jumpers, the peripheral substrate portion is provided with film bonding pads; while the central portion carries a film heater, a gas-sensitive film, and a film electrode for connecting with a circuit for measuring the electrical resistance of the gas-sensitive film: all these being electrically, connected to the bonding pads through film conductors located on the jumpers. According to the invention, the peripheral substrate portion is ring-shaped, the central portion thereof is shaped as a disk electrically connected to the peripheral portion by three jumpers spaced 120° apart, and the jumpers have branchings at an angle of 120° at the place of connection to the peripheral portion. The gas sensor device, as placed within an outer package, is designed to have geometry with relative spacings between its portions such that the ratio between the diameter of the central portion and the inside diameter of the peripheral portion is 0.2–0.4, and the ratio between the jumper length from the center of the circuit to the branching and the inside diameter of the peripheral portion is 0.6–0.8, while the width of the jumpers is 0.05–0.15 mm and the thickness of the jumpers and of the central substrate portion is 0.15–0.25 mm.

The film heater may be placed in a recess provided on the face surface of the central substrate portion.

It is desirable that the peripheral substrate portion has through holes and is fixed on a metal base of the package in such a manner that the internal package leads are arranged in the holes of the peripheral substrate portion and are electrically connected to the bonding pads, while the cover of the package has a hole to admit the medium under analyses.

Providing the ring-shaped peripheral substrate portion and the disk-shaped central substrate portion gives an additional rigidity to the films and circuit, integrated and reduces the stress level therein.

The interconnection of the peripheral substrate portion to the central substrate portion by three jumpers spaced 120° apart is selected so as to provide the heat insulation of the central substrate portion and to compensate optimally for any mechanical stresses arising upon heating the central substrate portion.

The fact that the ratio between the diameter of the central substrate portion and the inside diameter of the peripheral portion is design selected to be 0.2–0.4, and the ratio between the jumper length from the center of the circuit to the branching and the inside diameter of the peripheral portion to be 0.6–0.8, as well as design selection of the jumper width to be 0.05–0.15 mm and of the thickness of the jumpers and of the central substrate portion to be 0.15–0.25 is explained by the desire to attain optimal circuit geometry for suitable thermal insulation, according to the invention, from the viewpoint of the better heat insulation of the central substrate portion and the strength of the film circuit construction.

The upper limits of the value of the aforementioned ratios (0.4 and 0.8, respectively) are dictated by the permissible value of the heat resistance of the jumpers at which the temperature of the central substrate portion is within the required range for providing good selectivity in device performance, that results because a required level of heat insulation is provided.

The lower limits of the value of said ratios (0.2 and 0.6, respectively) are dictated by the permissible length of the jumpers at which the mechanical strength of the circuit construction remains unaffected.

BRIEF DESCRIPTION OF THE DRAWINGS

The present invention is further illustrated by a detailed description of some specific exemplary embodiments thereof to be taken with reference to the accompanying drawings, wherein.

BEST METHOD OF CARRYING OUT THE INVENTION

Figure 1:
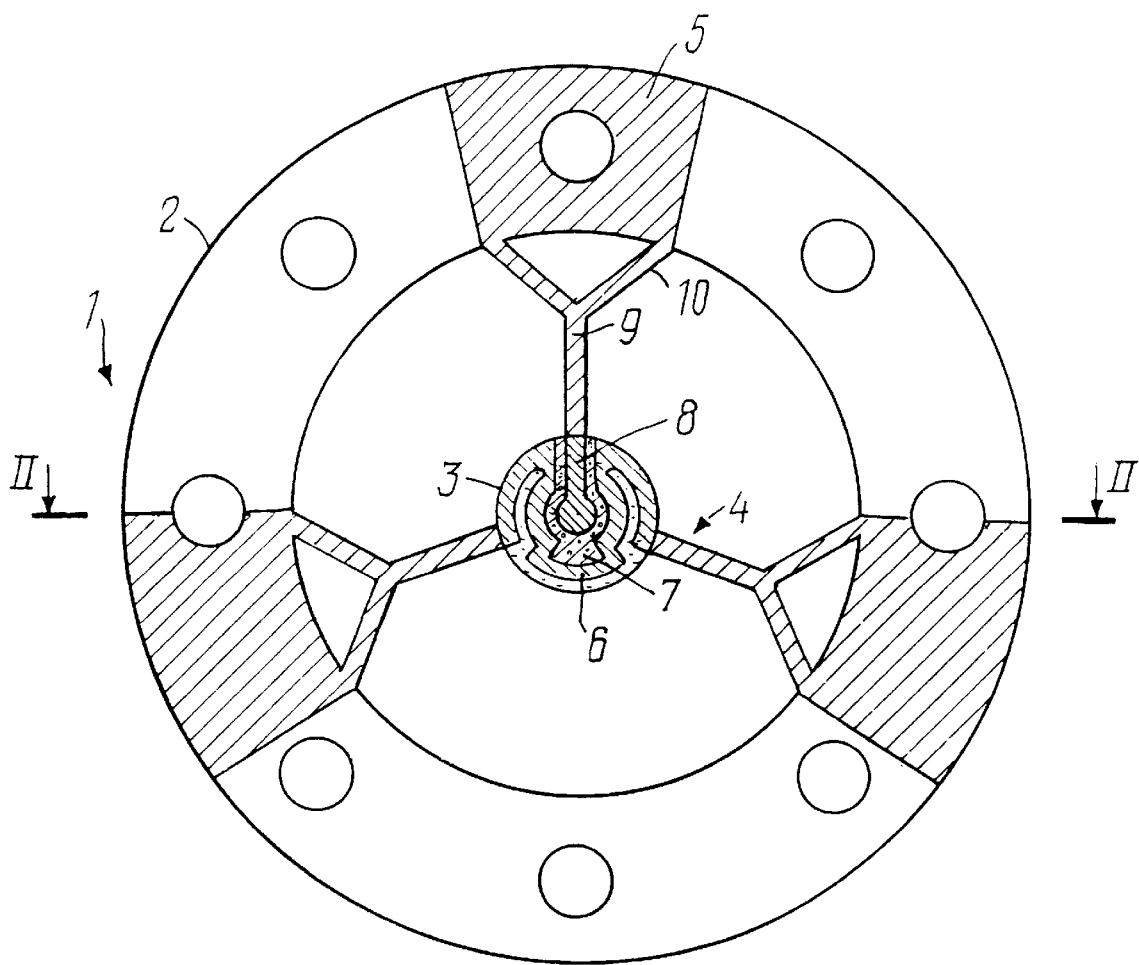
FIG. 1 is a plan view of the filed hybrid integrated circuit of a gas sensor.
Figure 2:
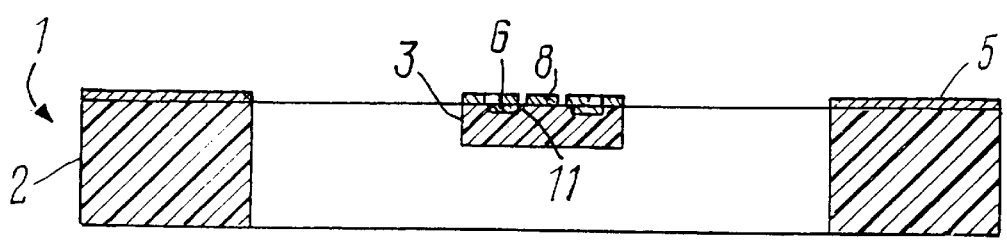
FIG. 2 is a section taken on the line II—II in FIG. 1.

The hybrid integrated circuit of a gas sensor for detecting $CH_4$, CO, and some other gases, according to the invention, comprises a substrate 1 (FIG. 1) made, e.g., of Polycor and being 0.5 mm thick, in the form of a mechanically strong peripheral portion 2 (FIGS. 1 and 2) shaped as a ring, e.g., 1.3 mm wide, and a central portion 3 shaped as a disk 1.2 mm in diameter thermally insulated from the peripheral portion 2. Both the peripheral portion 2 and the central portion 3 are joined up by jumpers 4 (FIG. 1) made of Polikor.

Figure 3:
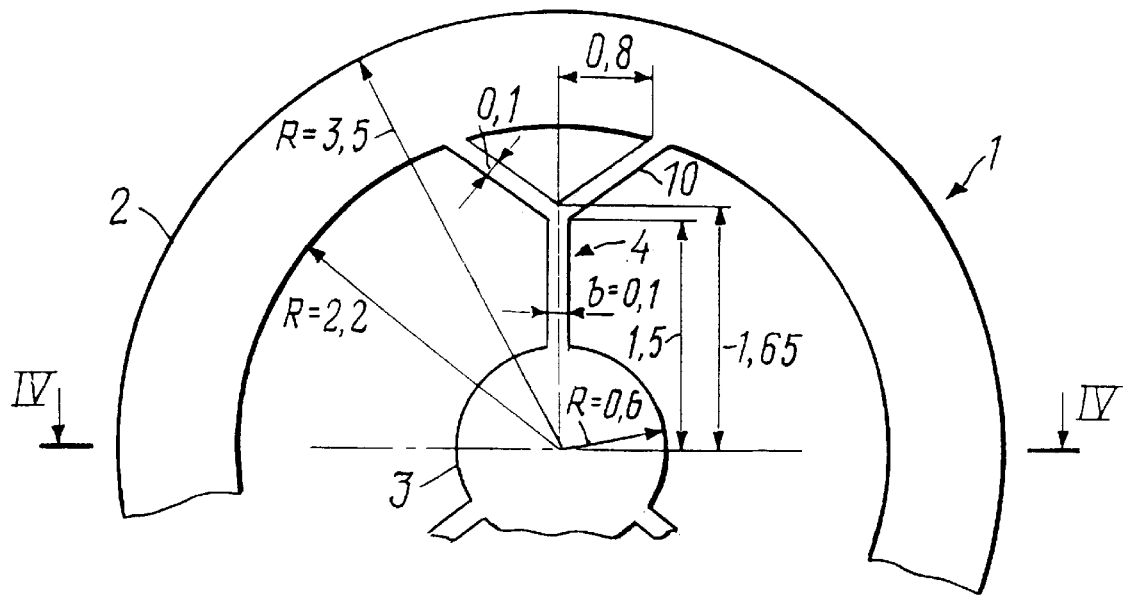
FIG. 3 is a view of FIG. 1 showing the respective dimensions of the circuit elements.
Figure 4:
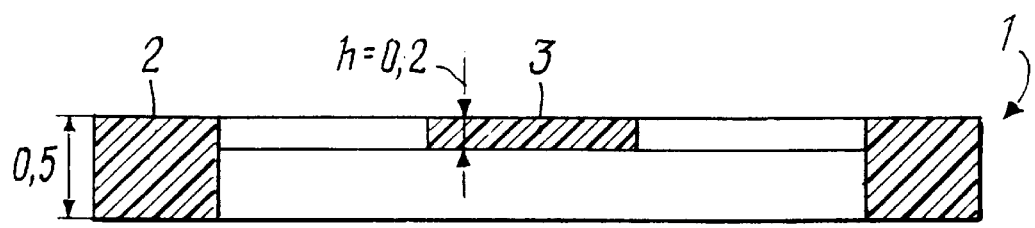
FIG. 4 is a section taken on the line V—V in FIG. 3.

The peripheral portion 2 of the substrate 1 is provided with film bonding pads 5 having the following structure: Ti (100 Ohm/sq.mm)—Au (5 µm). The central portion 3 of the substrate 1 carries a 200 Ohm 400 mW film heater 6 made of, e.g., a tantalum film, a gas-sensitive film 7 made of, e.g., $SnO_2$ with catalytic additives of MgO or CaO, Pd, Au, depending on the composition of the atmosphere being monitored, and a film electrode 8 having a structure similar to that of the bonding pad 5, a circuit for measuring the resistance of the gas-sensitive film 7 electrically connected to the bonding pads 5 by film conductors 9 provided on the jumpers 4 spaced 120° apart, and having branchings arranged at an angle of 120° at the place of connection to the peripheral portion 2. The ratio between the diameter of the central portion 3 and the inside diameter of the peripheral portion 2 is 0.2–0.4, and the ratio between the length of the jumper 4 from the center of the circuit to the branching 10 and the inside diameter of the peripheral portion 2 is 0.6–0.8 which is clearly evident from FIGS. 3 and 4. The width of the jumpers 4 is 0,1 mm and the thickness of the jumpers 4 and of the central portion 3 of the substrate 1 is 0,2 mm, which is dictated by better heat insulation of the central portion 3 with the circuit strength and durability remaining unaffected.

The heater 6 (FIG. 2) is established in a 10 µm deep recess 11 by filling it with a resistive paste followed by annealing at 800° C.

Figure 5:
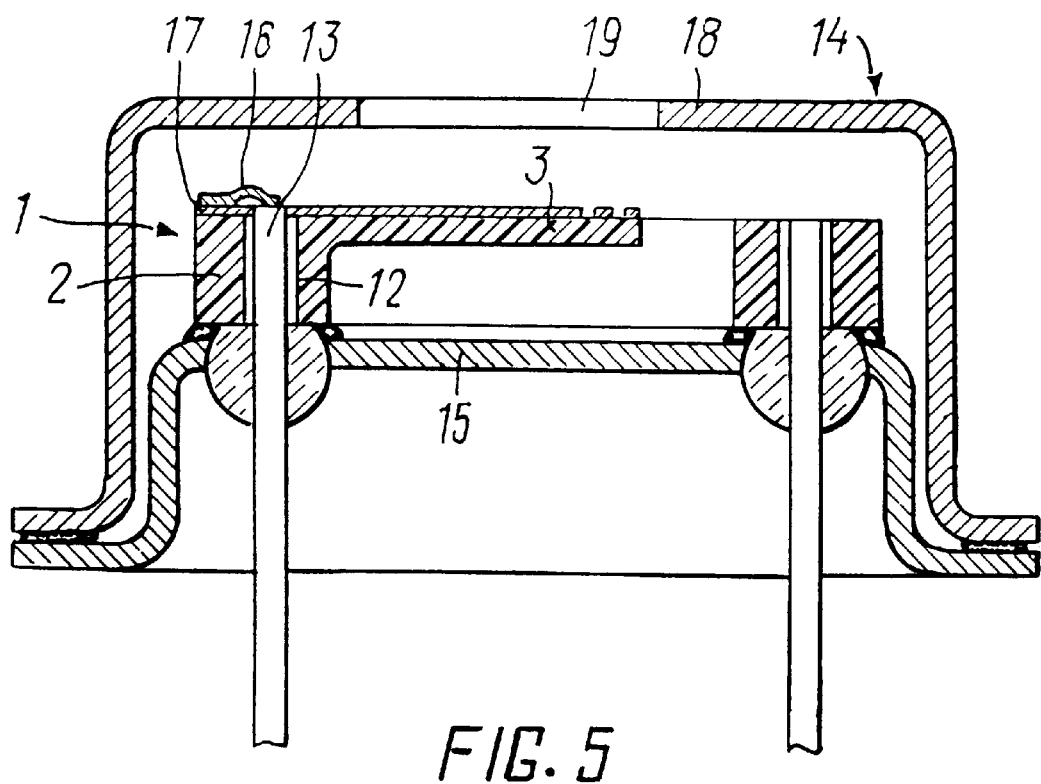
FIG. 5 is a sectional view of an alternative embodiment of the filed hybrid integrated circuit of a gas sensor.

The peripheral portion 2 (FIG. 5) of the substrate 1 has holes 12, e.g., 0.7 mm in diameter aligning with internal leads 13 of a package 14. The substrate 1 of the hybrid integrated circuit, according to the invention, is fixed on a metal base 15 of the package 14. The internal leads 13 of the package 14 are passed through the holes 12 in the peripheral portion 2 and are connected through a golden wire 16 to bonding pads 17 of the hybrid integrated circuit, according to the invention. A cover 18 of the package 14 has holes 19 which are 2 mm in diameter to admit the medium under analysis, e.g., air checked for presence of $CH_4$ closed by a soft net.

The circuit, according to the invention, functions as follows.

The film heater 6 (FIG. 1) delivers a supply voltage, e.g., 9 V, thus making possible heating the central portion 3 of the substrate 1 up to 300–500° C. and maintaining the preset temperature within an accuracy of ±5° C. Depending on the air impurity to be detected the temperature can be maintained at a preset level with the aforementioned accuracy. For instance, at 350° C. the sensor possesses an adequate selectivity and sensitivity to hydrogen, and so on. The resistance of the gas-sensitive film 7 is measured in the presence and in the absence of an air impurity, which enables a researcher to judge of the selectivity of the sensor.

Thus, the hybrid integrated circuit allows to increase the selectivity due to a more accurate maintaining the preset temperature which is in turn due to better heat insulation of the central portion 3 of the substrate 1. This is attained due to an optimized circuit construction as far as heat insulating and physical strength parameters thereof are concerned.

Moreover, the hybrid integrated circuit is simple in construction, whereby it is less laborious in efforts of manufacturing the claimed gas sensor structure.

In describing the disclosed embodiment of the present invention, specific narrow terminology is used for the sake of clarity. However, the invention is not restricted to the specific terms so selected, and it should be understood that each such term covers all equivalent elements functioning in a similar way and used for solving similar problems.

Although the present invention has been described herein with reference to the preferred embodiment, it will be understood that various modifications and alterations may occur to the details of construction without departing from the spirit and scope of the invention, as will be readily understood by those skilled in the art.

All these modifications and alterations should be considered to remain within the limits of the spirit and scope of the invention in accordance with the claims that follow.

INDUSTRIAL APPLICABILITY

The present invention can be used in designing, mounting and manufacturing a miniature gas concentration sensing transducer.

What is claimed is:

1. A hybrid integrated circuit of a gas sensor, comprising a substrate (1) in the form of a mechanically strong peripheral portion (2) and a central disk portion (3) thermally insulated therefrom, both portions being interconnected through a group of three jumpers (4) having a certain width and a special length chosen within a proper range, the peripheral portion (2) of the substrate (1) has a central opening characterized by an inside diameter circumference and is provided with a set of three film bonding pads (5), the central portion (3) fitting within said circumference carries a film heater (6), a gas-sensitive film (7), and a film electrode (8) of a circuit for measuring the resistance of the gas-sensitive film (7), all these components being electrically connected to the bonding pads (5) through film conductors (9) located on the jumpers (4), CHARACTERIZED in that the peripheral portion (2) of the substrate (1) is ring-shaped, the central portion (3) thereof is shaped as a disk electrically connected to the peripheral portion (2) by three jumpers (4) spaced 120° apart around the gas sensor, the three jumpers (4) have a triad of branchings (10) arranged at an angle spacing of 120° around the gas sensor at a circular set of three places of connection to the peripheral portion (2), the ratio between the diameter of the central portion (3) and the inside diameter of the peripheral portion (2) is 0.2–0.4, and the ratio between the length of the jumper (4) from the center of the circuit to the radius of the branchings (10) reaching said places of connection and the inside diameter of the peripheral portion (2) is 0.6–0.8, while the width of the jumpers (4) is 0.05–0.15 mm and the thickness of the jumpers (4) and of the central portion (3) of the substrate (1) is 0.15–0.25 mm.

2. The hybrid integrated circuit of a gas sensor as set forth in claim 1, wherein said central portion has a face surface and the film heater (6) is placed in a recess (11) provided on the face surface of the central portion (3) of the substrate (1).

3. The hybrid integrated circuit of a gas sensor as set forth in claim 1 wherein the peripheral portion (2) of the substrate (1) has through holes (12) and is fixed on a metal base (15) of a package (14) in such a manner that internal electrical leads (13) of the package (14) are arranged in the holes (12) of the peripheral portion (2) of the substrate (1) and are electrically connected to a subset of three bonding pads (17), and a cover (18) of the package (14) has holes (19) to admit the medium under analyses.

* * * * *